United States Patent [19]

Kataoka et al.

[11] Patent Number: 4,567,254

[45] Date of Patent: Jan. 28, 1986

[54] METHOD FOR PREPARING N⁶,8-DISUBSTITUTED 3',5'-CYCLIC ADENOSINE MONOPHOSPHATE AND SALT THEREOF

[75] Inventors: Shigehiro Kataoka; Takashi Nakamura; Nobuyuki Yamaji, all of Noda; Seiichi Nasuno, Nagareyama, all of Japan

[73] Assignee: Kikkoman Corporation, Japan

[21] Appl. No.: 652,093

[22] Filed: Sep. 19, 1984

[51] Int. Cl.⁴ .................. C07H 15/12; C07H 17/00
[52] U.S. Cl. ................................................. 536/27
[58] Field of Search ................................ 536/27

[56] References Cited

U.S. PATENT DOCUMENTS 3,856,776 12/1974 Cehovic et al. ................ 536/27
4,058,659 11/1977 Robins et al. .................. 536/27
4,458,067 7/1984 Yamaji et al. .................. 536/27

FOREIGN PATENT DOCUMENTS 0116298 7/1984 Japan ............................. 536/27
0227898 12/1984 Japan ............................. 536/27

OTHER PUBLICATIONS

Jon P. Miller et al, "Synthesis and Enzymatic and Inotropic Activity of Some New 8-Substituted and 6,8-Disubstituted Derivatives of Adenosine Cyclic 3',5'-Monophosphate," J. Med. Chem., 1980, 23, 242-251.
Boswell et al, Syntheses of 6,8-Disubstituted-9-β-D-Ribofuranosylpurine 3',5'-Cyclic Phosphates, J. Heterocyclic Chem., 12, 1 (1975).
Morrison et al., Organic Chemistry, pp. 740-741 (3d Ed., 1973).
Uesugi et al, Journ. Amer. Chem. Soc., 94:15 (1972) pp. 5480-5486.

*Primary Examiner*—Ethel G. Love
*Attorney, Agent, or Firm*—Banner, Birch, McKie & Beckett

[57] ABSTRACT

A method for preparing an N⁶,8-disubstituted 3',5'-cyclic adenosine monophosphate or a salt thereof represented by the general formula

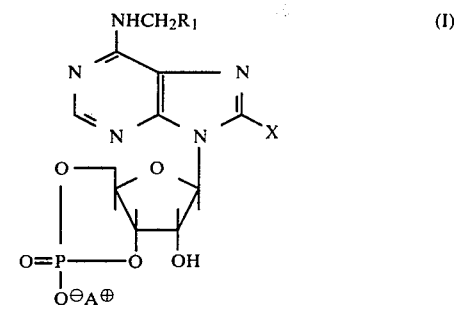

wherein X denotes a halogen atom or

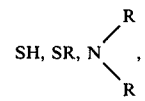

$N_3$, OH or OR, R being an alkyl or aralkyl group; $A^{\oplus}$ denotes a hydrogen ion, alkali metal ion, ammonium ion or organic ammonium ion; and $R_1$ denotes an alkyl or aromatic group, which method comprises reacting an 8-substituted 3',5'-cyclic adenosine monophosphate or a salt thereof represented by the general formula (II)

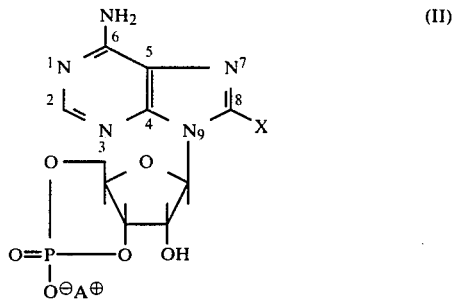

wherein X and $A^{\oplus}$ are as defined above, with an aldehyde represented by the general formula $R_1$—CHO    (III)

wherein $R_1$ is as defined above, to form an imine compound represented by the general formula

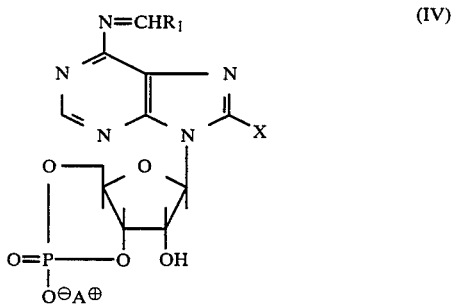

wherein X, $R_1$ and $A^{\oplus}$ are as defined above, as an intermediate, and then reducing the imine compound.

4 Claims, No Drawings

METHOD FOR PREPARING N⁶,8-DISUBSTITUTED 3',5'-CYCLIC ADENOSINE MONOPHOSPHATE AND SALT THEREOF

BACKGROUND OF THE INVENTION

1. Field of the Invention

This invention relates to a novel method for preparing an $N^6,8$-disubstituted 3',5'-cyclic adenosine monophosphate (hereinafter referred to as $N^6,8$-disubstituted CAMP) and a salt thereof.

2. Description of the Prior Art

CAMP and its derivatives have various physiological activities and are promising as medicinal agents in a variety of application fields. The $N^6,8$-disubstituted CAMP has excellent pharmacological activities including antiinflammative activity, inhibitory activity of platelet aggregation, hypotensive activity, cardiotonic activity and antitumor activity.

As the prior methods for preparing an $N^6,8$-disubstituted CAMP, there have been known a method wherein a 6-chloro-8-substituted 9-β-D-ribofuranosylpurine 3',5'-cyclic phosphate obtained by chlorination of the 6-position of 8-substituted inosine 3',5'-cyclic phosphate is reacted with an alkylamine [process I: U.S. Pat. No. 4,058,659; Journal of Medicinal Chemistry, 23, 242–251 (1980)], Process I

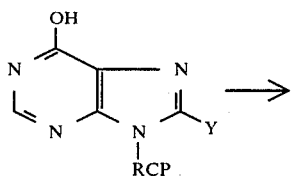

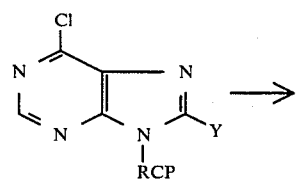

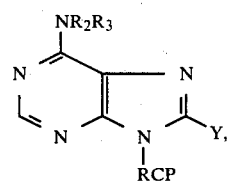

a method wherein CAMP is treated with an alkyl halide or the like to give an $N^1$-substituted CAMP, which is then converted, in an aqueous alkaline solution, via Dimroth rearrangement into an $N^6$-substituted CAMP, and the latter is brominated at the 8-position and then treated with nucleophiles such as alkylamine or thiol [process II: Journal of Medicinal Chemistry, 23, 242–251 (1980)], Process II

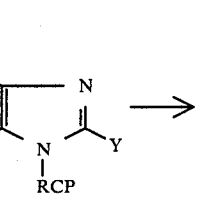

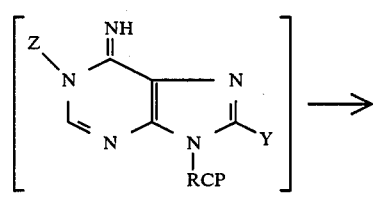

and further a method wherein 8-substituted CAMP is reacted with alkyl halide or the like, and the resulting $N^1,8$-disubstituted CAMP is subjected to Dimroth rearrangement in an aqueous alkaline solution (process III: U.S. Pat. No. 4,058,659), Process III -continued

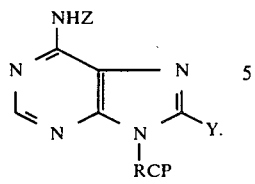

But all these methods have disadvantages of low yield, complicated process steps and long reaction time, and hence are unsatisfactory as industrial methods of preparation.

SUMMARY OF THE INVENTION

The present inventors made extensive studies to overcome the disadvantages mentioned above. As a result, it has been found out that an $N^6,8$-disubstituted CAMP or its salt (I) can be prepared with good efficiency by reacting an 8-substituted CAMP or its salt (II), which can be obtained by a simple procedure from CAMP as starting material, with an aldehyde and then reducing the resulting product.

The object of this invention is to provide a novel method for preparing an $N^6,8$-disubstituted CAMP or a salt thereof.

According to this invention, there is provided a method for preparing an $N^6,8$-disubstituted 3′,5′-cyclic adenosine monophosphate or a salt thereof represented by the general formula

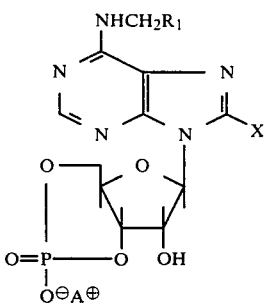 (I)

wherein X denotes a halogen atom or

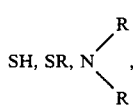

$N_3$, OH or OR, R being an alkyl or aralkyl group; $A^\oplus$ denotes a hydrogen ion, alkali metal ion, ammonium ion or organic ammonium ion; and $R_1$ denotes an alkyl or aromatic group, which method comprises reacting an 8-substituted 3′,5′-cyclic adenosine monophosphate or a salt thereof represented by the general formula (II)

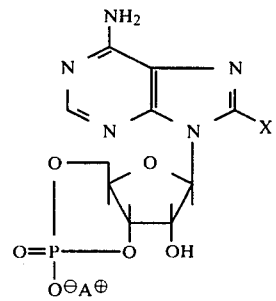 (II)

wherein X and $A^\oplus$ are as defined above, with an aldehyde represented by the general formula $R_1$—CHO (III)

wherein $R_1$ is as defined above, to form an imine compound represented by the general formula

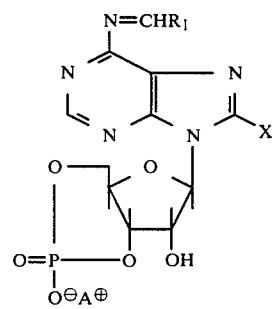 (IV)

wherein X, $R_1$ and $A^\oplus$ are as defined above, as an intermediate, and then reducing the imine compound.

DETAILED DESCRIPTION OF THE INVENTION

The 8-substituted CAMP represented by the general formula (II) or its salt used as the starting material of this invention can be prepared in a known method. For example, CAMP can be treated with bromine to give 8-bromo-CMAP; or the 8-bromo-CAMP can be treated with nucleophiles such as dialkylamine or sodium alkoxide to give corresponding 8-dialkylamino-CAMP, 8-alkoxy-CAMP and the like [Biochemistry, 10, 2390–2395 (1971)]. The salt of 8-substituted CAMP can be obtained by treating a free acid of 8-substituted CAMP in a known manner with an alkali metal ion or an organic amine. These salts of 8-substituted CMAP may also be used as the starting material in this invention.

Examples of the alkyl group denoted by R in the definition of X in the general formula (II) include methyl, ethyl, butyl, isobutyl, hexyl and octyl group; those of the aralkyl group include benzyl group.

Examples of the compound of the general formula (II) usable in this invention include the following: 8-bromo-CAMP, 8-chloro-CAMP, 8-mercapto-CAMP, 8-(methylthio)-CAMP, 8-(ethylthio)-CAMP, 8-(butylthio)-CAMP, 8-(isobutylthio)-CAMP, 8-(hexylthio)-CAMP, 8-(octylthio)-CAMP, 8-(benzylthio)-CAMP, 8-(dimethylamino)-CAMP, 8-(diethylamino)-CAMP, 8-(dipropylamino)-CAMP, 8-(diisopropylamino)-CAMP, 8-(dibutylamino)-CAMP, 8-(dihexylamino)-CAMP, 8-azido-CAMP, 8-hydroxy-CAMP, 8- methoxy-CAMP, 8-ethoxy-CAMP, 8-propoxy-CAMP, 8-butoxy-CAMP, 8-(hexyloxy)-CAMP, and 8-(octyloxy)-CAMP as well as sodium, potassium, ammonium, triethylamine and tributylamine salt thereof.

Preferable $R_1$ in the aldehyde represented by the general formula (III) includes an alkyl group having 1 to 17, particularly 1 to 13, carbon atoms of straight or branched chain such as methyl, ethyl, propyl, isopropyl, butyl, isobutyl, pentyl, isopentyl, hexyl, isohexyl, heptyl, octyl, nonyl, decyl, undecyl, tridecyl, pentadecyl and heptadecyl, as well as an aromatic group such as phenyl, methylphenyl, hydroxyphenyl, methoxyphenyl or chlorophenyl group or furyl group.

In practicing the present invention, first, the compound of the general formula (II) is reacted with the aldehyde of the general formula (III) to form the corresponding imine compound of the general formula (IV) as an intermediate. In general, this reaction is conducted preferably in a solvent. The solvents usable in the reaction include water, alcohols such as methanol and ethanol, ethers such as tetrahydrofuran and dioxane, amides such as dimethylformamide and dimethylacetamide, organic acids or their ester such as acetic acid, butyric acid, ethyl acetate and, halogenated hydrocarbons such as dichloromethane and chloroform. These solvents may be used either alone or in combination of two or more thereof. Preferred among these solvents are water, methanol, dioxane, dimethylformamide and acetic acid. The compound of the formula (II) and the aldehyde of the formula (III) may be reacted in equimolar proportion, but they may also be reacted by using excess of either of the components, preferably the aldehyde of the formula (III). Preferred amount of the aldehyde of the general formula (III) is 2 to 40 moles per 1 mole of the compound of the general formula (II). The pH of the reaction mixture may be selected in a wide range so long as it does not interfere with the formation of the imine compound, but a strongly alkaline region is rather unfavorable because of the possible danger of hydrolysis of the intermediate. The pH of the reaction mixture is therefore usually 7.0 or less.

The imine compound of the formula (IV) obtained above as the intermediate is then reduced to obtain the intended compound of the general formula (I). The reduction can be conducted by conventional methods of reduction. Methods which can be favorably used include one using a reducing agent, e.g. metal hydride such as sodium borohydride, sodium cyanoborohydride, lithium aluminum hydride or lithium aluminum cyanohydride, and borane; catalytic reduction using a catalyst such as nickel, iron, platinum and palladium; and reduction method using nascent hydrogen formed by treating a metal such as zinc, zinc amalgam, tin and iron with an acid such as acetic acid, hydrochloric acid and sulfuric acid. The above-mentioned solvents and solvent mixtures can also be used in the above reduction. When the reduction is conducted by using a metal hydride, it is preferable to add a dehydrating agent such as Molecular Sieves or acid anhydrides to the reaction system. Also, when a metal hydride is used, acidic conditions of pH 7 or less is preferable for promoting the reaction. The acids to be used for providing the acidic conditions include inorganic acids such as hydrogen chloride gas, hydrochloric acid, sulfuric acid and nitric acid; Lewis acids such as magnesium chloride and ammonium sulfate; and organic acids such as formic acid, acetic acid, propionic acid, butyric acid, benzoic acid, phthalic acid and p-toluene sulfonic acid.

According to a preferred embodiment of this invention, the reaction of the compound of the general formula (II) with the aldehyde of the general formula (III) is conducted under reductive conditions. Also in this case, the reaction conditions mentioned above are suitably used. The reaction to form the imine compound of the general formula (IV) and the reduction thereof can be conducted at $-20°$ C. to $120°$ C. usually at $10°$ to $50°$ C. The reaction time is 1 to 200 hours, preferably 2 to 100 hours.

The isolation and purification of the intended compound of the general formula (I) may be conducted by such purification method, used alone or in a suitable combination thereof, as column chromatography using silica gel, alumina, ion exchange resin or active carbon, recrystallization, precipitation by means of pH adjustment, salting out using sodium chloride, and extraction using an organic solvent. The free acid of the compound of the general formula (I) can be treated, for example, with hydroxide, carbonate or hydrogen carbonate of alkali or alkaline earth metal, ammonia, organic amine, e.g. tertiary amine such as triethylamine or tributylamine, to give a corresponding salt of the compound of the general formula (I) at the cyclic phosphate moiety.

Examples of the $N^6$,8-disubstituted CAMP of the general formula (I) or its salt obtainable according to this invention include the following: $N^6$-ethyl-8-bromo-CAMP, $N^6$-butyl-8-bromo-CAMP, $N^6$-octyl-8-bromo-CAMP, $N^6$-benzyl-8-bromo-CAMP, $N^6$-propyl-8-chloro-CAMP, $N^6$-decyl-8-chloro-CAMP, $N^6$-butyl-8-mercapto-CAMP, $N^6$-isobutyl-8-mercapto-CAMP, $N^6$-heptyl-8-mercapto-CAMP, $N^6$-benzyl-8-mercapto-CAMP, $N^6$-propyl-8-(methylthio)-CAMP, $N^6$-pentyl-8-(methylthio)-CAMP, $N^6$-furfuryl-8-(methylthio)-CMAP, $N^6$-octyl-8-(ethylthio)-CAMP, $N^6$-dodecyl-8-(ethylthio)-CAMP, $N^6$-propyl-8-(octylthio)-CAMP, $N^6$-pentyl-8-(octylthio)-CAMP, $N^6$-butyl-8-(benzylthio)-CAMP, $N^6$-dodecyl-8-(benzylthio)-CAMP, $N^6$-hexadecyl-8-(benzylthio)-CAMP, $N^6$-benzyl-8-(benzylthio)-CAMP, $N^6$-octyl-8-(dimethylamino)-CAMP, $N^6$-octadecyl-8-(dimethylamino)-CAMP, $N^6$-benzyl-8-(dimethylamino)-CAMP, $N^6$-furfuryl-8-(dimethylamino)-CAMP, $N^6$-ethyl-8-(dipropylamino)-CAMP, $N^6$-propyl-8-(diisopropylamino)-CAMP, $N^6$-pentyl-8-(dibutylamino)-CAMP, $N^6$-heptyl-8-azido-CAMP, $N^6$-decyl-8-azido-CAMP, $N^6$-tetradecyl-8-azido-CAMP, $N^6$-octyl-8-hydroxy-CAMP, $N^6$-hexadecyl-8-hydroxy-CAMP, $N^6$-isobutyl-8-methoxy-CAMP, $N^6$-dodecyl-8-methoxy-CAMP, $N^6$-benzyl-8-methoxy-CAMP, $N^6$-octyl-8-(hexyloxy)-CAMP, and $N^6$-benzyl-8-(hexyloxy)-CAMP as well as alkali metal salts, ammonium salts and organic ammonium salts thereof.

This invention will be described in more detail below with reference to Examples, but it is not limited thereto.

EXAMPLE 1

Preparation of ammonium salt of $N^6$-ethyl-8-bromo-CAMP (A) To a solution of 8.0 g of CAMP in 14 ml of 2N NaOH solution, were added 120 ml of 1M acetate buffer solution, pH 3.9, and 2 ml of bromine, and the mixture was allowed to react at room temperature for 16 hours with stirring. After completion of the reaction, the precipitated crystals were separated by filtration to give 8.2 g of 8-Br-CAMP, mp $209°–210°$ C. (decomp.).

(B) To 3.0 g of 8-Br-CAMP, were added 10 ml of water and 30 ml of methanol followed by 2 ml of tri-n-butylamine, and the mixture was stirred at room temperature to form a solution. The solution was evaporated to dryness under reduced pressure to give 4.2 g of tri-n-butylamine salt of 8-Br-CAMP.

(C) Into 5 ml of methanol was dissolved 600 mg of tributylamine salt of 8-Br-CAMP, and the resulting solution was mixed with 1.5 ml of acetic acid, 0.1 ml of acetic anhydride and 0.6 ml of acetaldehyde, then further with 100 mg of sodium cyanoborohydride, and the mixture was stirred at room temperature for 1.5 hours. To the mixture was further added 102 mg of sodium cyanoborohydride at every 2 hours, 3 times in all. The mixture was stirred overnight and then mixed with a small amount of water. After removal of the solvent from the resulting mixture under reduced pressure, the remaining oily substance was dissolved in a small amount of water. The solution was adjusted to pH 2 by addition of 2N hydrochloric acid and then adsorbed on a charcoal column (1.5×17 cm). After washed with water, the column was eluted with methanol-water-28% ammonium hydroide mixture (20:10:1 by volume). The eluted fractions were collected and evaporated to dryness under reduced pressure.

The caramel-like substance obtained was dissolved in a small amount of methanol, and separated and purified by silica gel thin-layer chromatography (developing solvent:methanol-chloroform mixture 35:75 by volume). The part of the thin layer showing the UV absorption band of the intended compound (Rf value in the vicinity of 0.12) was scraped out, and extracted with methanol. The extract was evaporated to dryness under reduced pressure to give 439 mg (69% yield) of ammonium salt of $N^6$-ethyl-8-bromo-CAMP, mp 201°–204° C. (decomp.).

| UV: $\lambda_{max}^{0.1\ N-HCl}$ | 267 nm |
|---|---|
| $\lambda_{max}^{0.1\ N-NaOH}$ | 270 nm |

EXAMPLE 2

Preparation of sodium salt of $N^6$-butyl-8-bromo-CAMP

To 1.3 g of sodium salt of 8-bromo-CAMP were added 3 ml of acetic acid and 10 ml of methanol, and the mixture was stirred to form a solution. To the resulting reaction solution were added 3 ml of n-butyraldehyde and 230 mg of sodium cyanoborohydride, and the mixture was stirred overnight at room temperature. To the mixture, then, were further added, at every 5 hours, 150 mg, 195 mg and 195 mg of sodium cyanoborohydride in succession. The mixture was stirred overnight, and then mixed with a small amount of water. The solvent was distilled off from the mixture under reduced pressure, and the residue was dissolved in a small amount of water. The solution was mixed with 2N hydrochloric acid and the adsorbed on a charcoal column (2.2×17.5 cm). After being washed with water, the column was eluted with methanol-water-28% ammonium hydroxide mixture (20:10:1 by volume). The eluted fractions were collected and evaporated to dryness under reduced pressure. The resulting residue was dissolved in 1N NaOH solution, mixed with 3 g of silica gel, and then evaporated under reduced pressure to remove the solvent. The residue obtained was placed on the top surface of a silica gel column and then eluted with methanol-chloroform mixture by the methanol concentration gradient method. The fractions eluted with 15–30% by volume methanol concentration in chloroform containing the intended compound were collected and evaporated to dryness under reduced pressure to give 985 mg (67% yield) of sodium salt of $N^6$-butyl-8-bromo-CAMP, mp 242°–248° C. (decomp.).

| UV: $\lambda_{max}^{0.1\ N-HCl}$ | 270 nm |
|---|---|
| $\lambda_{max}^{0.1\ N-NaOH}$ | 273 nm |

EXAMPLE 3-A

Preparation of $N^6$-butyl-8-mercapto-CAMP

To 2.0 g of 8-mercapto-CAMP neutralized and dissolved in 1N NaOH solution, were added 5 ml of 5M acetate buffer solution (pH 3.9), 5 ml of acetic acid, 5 ml of ethanol, 3 ml of n-butyraldehyde, 500 mg of zinc dust and 100 mg of copper sulfate, and the mixture was heated to 80° C. To the mixture were then added 500 mg of zinc dust after 1 hour, 1.5 ml of n-butyraldehyde as well as 500 mg of zinc dust after 7 hours from the beginning of reaction, and 200 mg of copper sulfate as well as 500 mg of zinc dust after 8 hours, and the mixture was allowed to react overnight at 80° C. The reaction mixture was separated by filtration and the residue was washed with methanol and water. The washings were combined with the filtrate and then concentrated. The concentrate was mixed with a small amount of water and 2N hydrochloric acid, and adsorbed on a charcoal column (1.8×20 cm). After being washed with water, the column was eluted with ethanol-water-28% ammonium hydroxide mixture (10:10:1 by volume) and the eluted fractions were concentrated. The concentrate was adjusted to pH 2 by addition of 2N hydrochloric acid and the formed precipitate was filtered and dried to give 1.1 g (49% yield) of $N^6$-butyl-8-mercapto-CAMP, mp 211°–218° C. (decomp.).

| UV: $\lambda_{max}^{0.1\ N-HCl}$ | 228.5, 245 (shoulder), 306 (shoulder), 315 nm |
|---|---|
| $\lambda_{max}^{0.1\ N-NaOH}$ | 233, 301 nm |

EXAMPLE 3-B

Preparation of $N^6$-butyl-8-mercapto-CAMP

To 10 ml of acetic acid containing 160 mg of anhydrous sodium acetate, was added 543 mg of 8-thiobenzyl CAMP, and the mixture was stirred for 10 minutes at 120° C. to form a solution. The resulting reaction mixture was cooled to room temperature, and then mixed with 2 ml of n-butyraldehyde and 120 mg of sodium cyanoborohydride, and stirred at room temperature. To the mixture, then, were further added sodium cyanoborohydride in a proportion of 70 mg, 70 mg, 60 mg and 60 mg at after 2, 5, 7 and 9 hours, respectively. The mixture was stirred further for overnight, and then mixed with a small amount of water. The solvent was distilled off from the mixture under reduced pressure, and the resulting oily residue was dissolved in a small amount of water. The solution was adjusted to pH 2 by addition of 2N hydrochloric acid and then adsorbed on a charcoal column (1.8×15 cm). After being washed with water, the column was eluted with methanol-water-28% ammonium hydroxide mixture (20:10:1 by volume). The eluted fractions were collected and evaporated to dryness under reduced pressure. The resulting residue was dissolved in 1N NaOH solution, mixed with 1.5 g of silica gel, and then evaporated to remove the solvent. The resulting residue was placed on the top surface of a silica gel column and then eluted with methanol-chloroform mixture (20–30% methanol in chloroform by volume). The fractions of methanol-chloroform mixture (25:75 by volume) containing the intended compound were collected and evaporated to dryness under reduced pressure. The resulting residue was dissolved in a small amount of water and adjusted to pH 2 by addition of 2N hydrochloric acid, and the formed precipitate was filtered and dried to give 432 mg (69% yield) of N[6]-butyl-8-mercapto-CAMP.

EXAMPLE 4

Preparation of N[6]-butyl-8-(thiobenzyl)-CAMP

In a mixture 12 ml of methanol, 3 ml of acetic acid and 0.2 ml of acetic anhydride, was added 950 mg of sodium salt of 8-(thiobenzyl)-CAMP and dissolved with stirring. To the solution was added 3 ml of n-butyraldehyde followed by 145 mg of sodium cyanoborohydride, and the mixture was stirred at room temperature. The mixture was mixed, after 6 hours, with 130 mg and, after 27 hours, with additional 100 mg of sodium cyanoborohydride, and was stirred for one more day. The reaction mixture was mixed with a small amount of water, and the solvent was evaporated off under reduced pressure. The remaining caramel-like substance was dissolved in water-methanol mixture and adjusted to pH 2 with 2N hydrochloric acid to give 593.4 mg of N[6]-butyl-8-(thiobenzyl)-CAMP. Further, the mother liquor was mixed with 2.5 g of silica gel, and the solvent was evaporated off under reduced pressure. The resulting residue was placed on the top surface of the silica gel column and then eluted with methanol-chloroform mixture by the methanol concentration gradient method. The fraction eluted with 10% methanol in chloroform mixture (1:9 by volume) containing the intended compound was evaporated to dryness under reduced pressure to give 143.7 mg of N[6]-butyl-8-(thiobenzyl)-CAMP. The total yield of the intended compound was 737.1 mg, corresponding to 72.4% yield. mp: 168°–170° C.

| UV: $\lambda_{max}^{0.1\ N-HCl}$ | 289 nm |
|---|---|
| $\lambda_{max}^{0.1\ N-NaOH}$ | 292 nm |

EXAMPLE 5

Preparation of N[6]-dodecyl-8-(thiobenzyl)-CAMP

To 709 mg of sodium salt of 8-(thiobenzyl)-CAMP were added 15 ml of methanol and 3.5 ml of acetic acid, and the mixture was stirred to form a solution. The solution was mixed with 2.8 g of laurylaldehyde and 10 ml of chloroform, stirred, then mixed with 95 mg of sodium cyanoborohydride, and stirred at room temperature. The mixture was further mixed, after 1 day, with 140 mg and, after 3 days, with additional 156 mg of sodium cyanoborohydride, and stirred for one more day. The reaction mixture was mixed with a small amount of water and evaporated under reduced pressure to remove the solvents. The residue was suspended in a small amount of water, mixed with 2N hydrochloric acid and adsorbed on a charcoal column (1.8×27 cm). After being washed with water, the column was eluted, and the fraction eluted with methanol-water-28% ammonium hydroxide mixture (20:10:1 by volume) was evaporated to dryness under reduced pressure. The residue obtained was mixed with methanol and filtered to remove the insolubles. The filtrate was concentrated and then subjected to silica gel thin-layer chromatography (developing solvent:methanol-chloroform mixture, 3:7 by volume) to effect separation and purification. Then, the part of the thin layer showing the UV absorption band of the intended compound (Rf value in the vicinity of 0.27) was scraped out and extracted with methanol. The extract was evaporated to dryness under reduced pressure, redissolved in water-methanol mixture (1:2 by volume) and adjusted to pH 2 with 2N hydrochloric acid to give 490 mg (53% yield) of N[6]-dodecyl-8-(thiobenzyl)-CAMP, mp 174°–177° C. (decomp.).

| UV: $\lambda_{max}^{EtOH}$ | 289.5 nm |
|---|---|
| $\lambda_{max}^{EtOH-HCl}$ | 289 nm |

EXAMPLE 6

Preparation of N[6]-isobutyl-8-methoxy-CAMP

To 690 mg of triethylamine salt of 8-methoxy-CAMP, were added 5 ml of methanol, 2 ml of acetic acid and 0.15 ml of acetic anhydride, and the mixture was stirred to form a solution. The solution was mixed with 1.36 ml of isobutyraldehyde and 105 mg of sodium cyanoborohydride, and stirred at room temperature. The mixture was mixed twice, at after 4 hours and 8 hours with 102 mg and, after 22 hours from the beginning of reaction, with additional 70 mg of sodium cyanoborohydride, and stirred for further 24 hours. The reaction mixture was mixed with a small amount of water and evaporated under reduced pressure to remove the solvents. The residue was dissolved in a small amount of water, mixed with 2N hydrochloric acid, and then adsorbed on a charcoal column (1.8×17 cm). After being washed with water, the column was eluted, and the fraction eluted with methanol-water-28% ammonium hydroxide mixture (20:10:1 by volume) was evaporated to dryness under reduced pressure. The residue obtained was dissolved in a small amount of methanol and subjected to silica gel thin-layer chromatography (developing solvent:methanol-chloroform mixture, 3:7 by volume) to effect separation and purification. The part of the thin layer showing the UV absorption band of the intended compound (Rf value in the vicinity of 0.13) was scraped out, extracted with methanol and the extract was evaporated to dryness under reduced pressure. The residue was dissolved in water-ethanol mixture, (1:1 by volume), and adjusted to pH 2 with 2N hydrochloric acid to give 331 mg (54% yield) of N[6]-isobutyl-8-methoxy-CAMP, mp. 221°–226° C. (decomp.).

| UV: $\lambda_{max}^{0.1\ N-HCl}$ | 265.5 nm |
|---|---|
| $\lambda_{max}^{0.1\ N-NaOH}$ | 265 nm |

EXAMPLE 7

Preparation of N⁶-octyl-8-hydroxy-CAMP

To 102 mg of triethylamine salt of 8-hydroxy-CAMP, was added 3 ml of acetic acid, and the mixture was stirred to form a solution. The solution was mixed with 0.36 ml of n-octylaldehyde and 24 mg of sodium borohydride, and stirred at room temperature. The mixture was mixed, after 30 minutes, with 15 mg, and, after 1 hour, with additional 11 mg of sodium borohydride and stirred for further 2 hours. The reaction mixture was mixed with a small amount of water, and evaporated under reduced pressure to remove the solvents. The residue was dissolved in a small amount of water, mixed with 2N hydrochloric acid, and adsorbed on a charcoal column (1.2×13 cm). After being washed with water the column was eluted, and the fraction eluted with methanol-water-28% ammonium hydroxide mixture (20:10:1 by volume) was evaporated to dryness under reduced pressure. The residue was dissolved in water, mixed with methanol, and adjusted to pH 2 with 2N hydrochloric acid and the formed precipitate was filtered and dried to give 74.6 mg (71.3% yield) of N⁶-octyl-8-hydroxy-CAMP, mp 210°–215° C. (decomp.).

| UV: $\lambda_{max}^{0.1\ N-HCl}$ | 272, 300 (shoulder) nm |
|---|---|
| $\lambda_{max}^{0.1\ N-NaOH}$ | 283 nm |

EXAMPLE 8

Preparation of N⁶-benzyl-8-(dimethylamino)-CAMP

To 638 mg of triethylamine salt of 8-(dimethylamino)-CAMP, were added 5 ml of methanol and 1.5 ml of acetic acid, and the mixture was stirred to form a solution. The solution was mixed with 1.4 ml of benzaldehyde and 132 mg of sodium cyanoborohydride and stirred at room temperature. The mixture was then mixed, after 4 hours, with 91 mg, then, after 17.5 hours, with 70 mg and, after 26.5 hours from the beginning of reaction, with additional 97 mg of sodium cyanoborohydride, and stirred for further 2 hours. The reaction solution was mixed with a small amount of water and evaporated under reduced pressure to remove the solvents. The residue thus obtained was dissolved in a small amount of water, adjusted to pH 2 by the addition of 2N hydrochloric acid, and adsorbed on a charcoal column (1.8×21 cm). After being washed with water, the column was eluted with methanol-water-28% ammonium hydroxide mixture (20:10:1 by volume), and the eluted fraction was evaporated to dryness under reduced pressure. The residue obtained was dissolved in a small amount of methanol, and subjected to silica gel thin-layer chromatography (developing solvent:methanol-chloroform mixture, 3:7 by volume) to effect separation and purification. The part of the thin layer showing the UV absorption band of the intended compound (Rf value in the vicinity of 0.18) was scraped out and extracted with methanol. The extract was evaporated to dryness under reduced pressure. The residue was dissolved in water-ethanol mixture, (1:1 by volume), and the solution was adjusted to pH 2 with 2N hydrochloric acid and the formed precipitate was filtered and dried to give 427 mg (68.5% yield) of N⁶-benzyl-8-(dimethylamino)-CAMP, mp 198°–202° C. (decomp.).

| UV: $\lambda_{max}^{0.1\ N-HCl}$ | 286 nm |
|---|---|
| $\lambda_{max}^{0.1\ N-NaOH}$ | 281 nm |

EXAMPLE 9

Preparation of N⁶-furfuryl-8-(dimethylamino)-CAMP

To 840 mg of triethylamine salt of 8-(dimethylamino)-CAMP, were added 10 ml of methanol and 2.5 ml of acetic acid, and the mixture was stirred to form a solution. The solution was mixed with 1.45 ml of furfural and 59 mg of sodium cyanoborohydride and stirred at room temperature for 0.5 hour. The mixture was then mixed with 50 mg each portion, three times, at every 40 minutes, and, after further 3.5 hours, with additional 56 mg of sodium cyanoborohydride, and stirred overnight. The mixture was then mixed with a small amount of water, and evaporated under reduced pressure to remove the solvents. The residue obtained was dissolved in a small amount of water, mixed with 2N hydrochloric acid, and adsorbed on a charcoal column (1.8×18 cm). After being washed with water, the column was eluted, and the fraction eluted with methanol-water-28% ammonium hydroxide mixture (20:10:1 by volume) was evaporated to dryness under reduced pressure. The residue obtained was dissolved in a small amount of methanol and subjected to silica gel thin-layer chromatography (developing solvent:methanol-chloroform mixture, 3:7 by volume) to effect separation and purification. The part of the thin layer showing the UV absorption band of the intended compound (Rf value in the vicinity of 0.17) was scraped out, extracted with methanol, and the extract was evaporated to dryness under reduced pressure. The residue obtained was dissolved in water. The solution was adjusted to pH 2 by the addition of 2N hydrochloric acid, mixed with 1 g of silica gel, and evaporated under reduced pressure to remove the solvents. The resulting residue was placed on the top of a silica gel column and eluted with methanol-chloroform mixture. The methanol-chloroform mixture (1:9 by volume) fractions containing the intended compound were collected and evaporated to dryness under reduced pressure to give 632.2 mg (79% yield) of N⁶-furfuryl-8-(dimethylamino)-CAMP. It was then recrystallized from ethanol-ether mixture. mp 204°–210° C. (decomp.).

| UV: $\lambda_{max}^{0.1\ N-HCl}$ | 285 nm |
|---|---|
| $\lambda_{max}^{0.1\ N-NaOH}$ | 279.5 nm |

What is claimed is:

1. A method for preparing an N⁶,8-disubstituted 3′,5′-cyclic adenosine monophosphate or salt thereof represented by the general formula

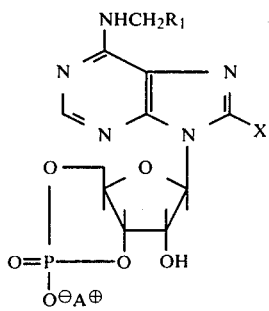

wherein X denotes a halogen atom, or

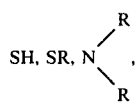

$N_3$, OH or OR, R being a methyl, ethyl, butyl, isobutyl, hexyl, octyl or benzyl group; $A^\oplus$ denotes a hydrogen ion, alkali metal ion, ammonium ion or organic ammonium ion; and $R_1$ denotes a methyl, ethyl, propyl, isopropyl, butyl, isobutyl, pentyl, isopentyl, hexyl, isohexyl, heptyl, octyl, nonyl, decyl, undecyl, tridecyl, phenyl, methylphenyl, hydroxiphenyl, methoxyphenyl, chlorophenyl or furyl group, which method comprises reacting 8-substituted 3',5'-cyclic adenosine monophosphate or salt thereof represented by the general formula (II)

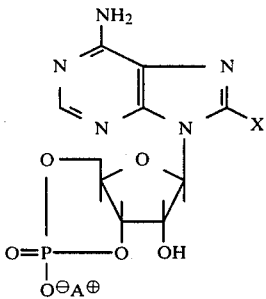

wherein X and $A^\oplus$ are as defined above, with an aldehyde represented by the general formula

 (III)

wherein $R_1$ is as defined above, in a solvent at a pH of 7.0 or less and at a temperature of $-20°$ to $120°$ C., the molar ratio of (II) to (III) being in the range of 1:2 to 1:40 to form an imine compound represented by the general formula

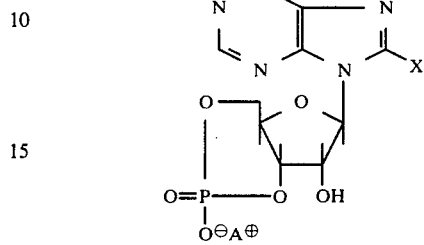

wherein X, $R_1$ and $A^\oplus$ are as defined above, as an intermediate, and reducing the imine compound in the presence of a metal hydride, nascient hydrogen or a catalyst of nickel, iron, platinum or palladium at a temperature in the range of $-20°$ to $120°$ C., said reaction of the compound of the general formula (II) with the aldehyde of the general formula (III) to form the imine compound of formula (IV) and said reduction thereof to the compound of the general formula (I) being conducted for a period of time between about 1 to 200 hours.

2. A method according to claim 1, wherein the formula (I) compound is isolated and purified by a method selected from the group consisting of (i) column chromatography using silica gel, alumina, ion exchange resin or active carbon; (ii) recrystallization; (iii) precipitation by means of pH adjustment; (iv) salting out using sodium chloride; (v) extraction using an organic solvent; or (vi) a combination thereof.

3. A method according to claim 1 wherein the reaction of the compound of the general formula (II) with the compound of the general formula (III) to form the imine compound and said reduction thereof to the compound of the general formula (I) is conducted at a temperature in the range of $10°$ to $50°$ C. and for a period of time of between about 2 to 100 hours.

4. A method according to claim 1, wherein the solvent is water, methanol, ethanol, tetrahydrofuran, dioxane, dimethylformamide, dimethylacetamide, butyric acid, acetic acid, ethyl acetate, dichloromethane and chloroform each alone or in combination of two or more thereof.

* * * * *